United States Patent [19]
Crittenden et al.

[11] Patent Number: 5,102,390
[45] Date of Patent: Apr. 7, 1992

[54] MICRODILATATION PROBE AND SYSTEM FOR PERFORMING ANGIOPLASTY IN HIGHLY STENOSED BLOOD VESSELS

[75] Inventors: James F. Crittenden, Hollis, N.H.; James J. Frassica, Chelmsford, Mass.

[73] Assignee: C. R. Bard, Inc., Murray Hill, N.J.

[21] Appl. No.: 729,541

[22] Filed: May 2, 1985

[51] Int. Cl.$^5$ ............................................. A61M 29/00
[52] U.S. Cl. ..................................... 604/96; 604/101; 606/192; 606/194
[58] Field of Search ............. 128/344, 348.1, 656–658; 604/95–103; 606/192, 194

[56] References Cited

U.S. PATENT DOCUMENTS

| | | | |
|---|---|---|---|
| 3,467,102 | 9/1969 | Fogarty et al. | 128/348 |
| 3,789,841 | 2/1974 | Antoshkiw | 128/2.05 R |
| 3,978,863 | 9/1976 | Fettel et al. | 128/348 |
| 4,195,637 | 4/1980 | Gruntzig et al. | 128/348 |
| 4,198,981 | 4/1980 | Sinnreich | 128/344 |
| 4,273,128 | 6/1981 | Lary | 128/305 |
| 4,292,974 | 10/1981 | Fogarty et al. | 128/344 |
| 4,307,722 | 12/1981 | Evans | 128/344 |
| 4,315,512 | 2/1982 | Fogarty | 128/344 |
| 4,323,071 | 4/1982 | Simpson et al. | 128/343 |
| 4,327,720 | 5/1982 | Bronson et al. | 128/207.15 |
| 4,338,942 | 7/1982 | Fogarty | 128/344 |
| 4,346,698 | 8/1982 | Hanson et al. | 128/1 D |
| 4,362,150 | 12/1982 | Lombardi, Jr. et al. | 128/1 D |
| 4,404,971 | 9/1983 | LeVeen et al. | 128/348.1 |
| 4,444,188 | 4/1984 | Bazell et al. | 128/344 X |
| 4,445,892 | 5/1984 | Hussein et al. | 128/344 X |
| 4,456,000 | 6/1984 | Schjeldahl et al. | 128/1 D |
| 4,561,439 | 12/1985 | Bishop et al. | 128/348.1 |
| 4,582,181 | 4/1986 | Sampson | 128/348.1 |
| 4,630,609 | 12/1986 | Chin | 128/344 |
| 4,714,460 | 12/1987 | Calderon | 604/28 |

FOREIGN PATENT DOCUMENTS 654214 2/1986 Switzerland.

Primary Examiner—John D. Yasko
Assistant Examiner—Anthony Gutowski
Attorney, Agent, or Firm—Wolf, Greenfield & Sacks

[57] ABSTRACT

A balloon angioplasty system includes a balloon dilatation catheter having an inflation and deflation lumen for the balloon and a main lumen extending the full length of the catheter to provide fluid communication from the proximal to the distal end of the catheter. A microdilatation probe has a small diameter and can be passed through the main lumen of the dilatation catheter. The microdilatation probe has a balloon at its distal end which is collapsible to enable it to be passed through the main lumen of the dilatation catheter so that it can be projected distally beyond the distal tip of the dilatation catheter. The probe balloon is inflatable to a diameter no smaller than the diameter of the uninflated dilatation catheter. The probe and dilatation catheter are constructed so that fluid communication is maintained through the main lumen of the dilatation catheter while the microdilatation probe extends through the catheter thereby enabling liquids to be infused and pressure measurements to be taken while the probe is in place. The probe may include a distal tip which can hold a preset curve.

In use, a stenosis which cannot be crossed by the dilatation catheter may be enlarged sufficiently to permit passage of the dilatation catheter by first projecting the dilatation probe into the stenosis, then inflating the probe balloon to enlarge the lumen of the stenosis sufficiently to thereafter receive the dilatation catheter.

28 Claims, 3 Drawing Sheets

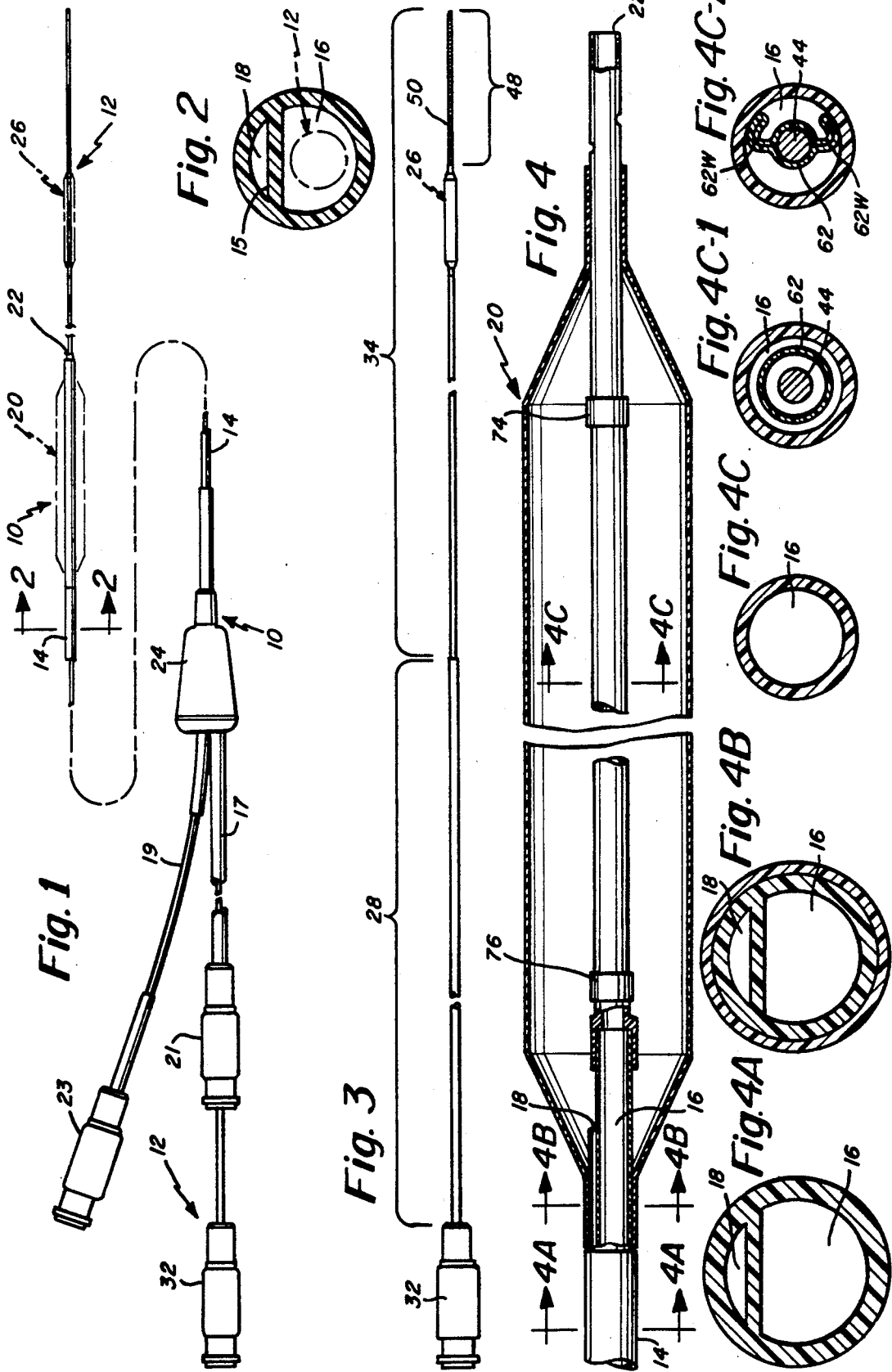

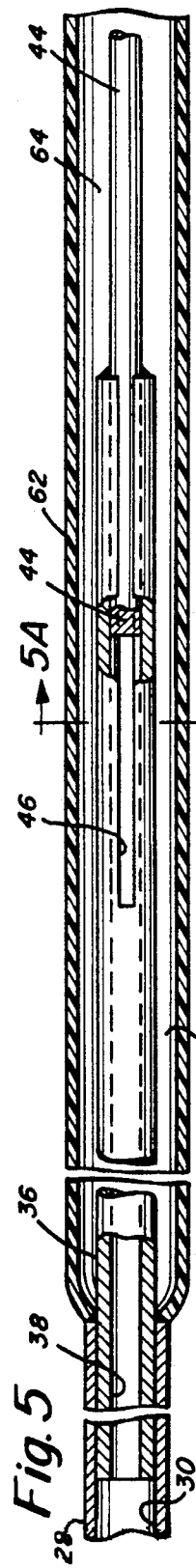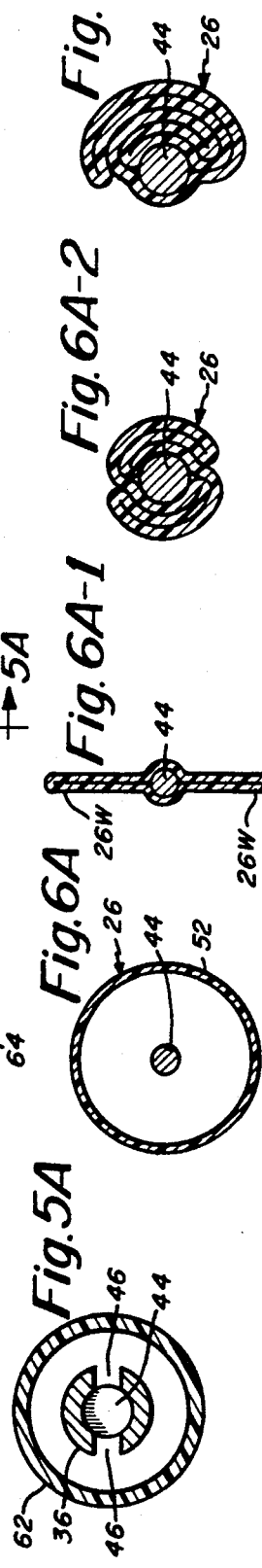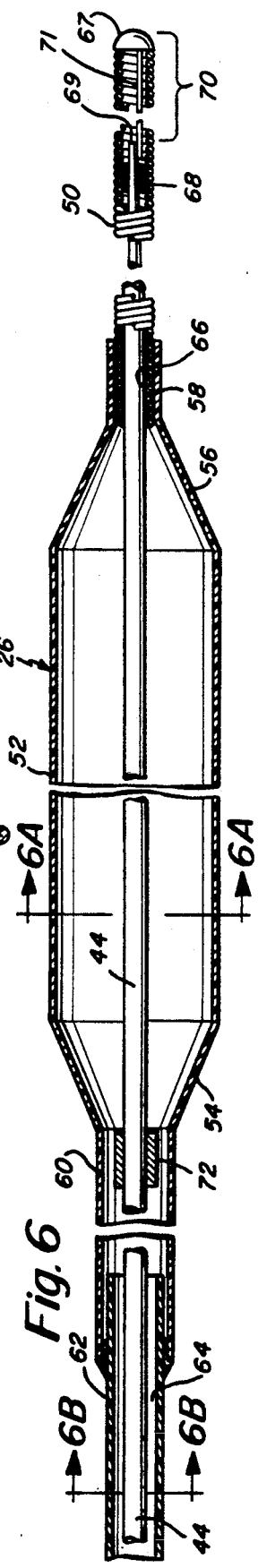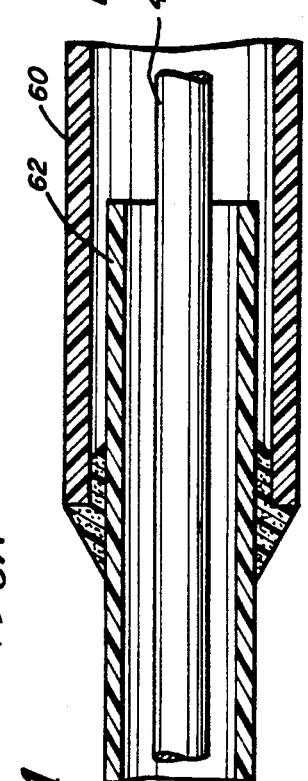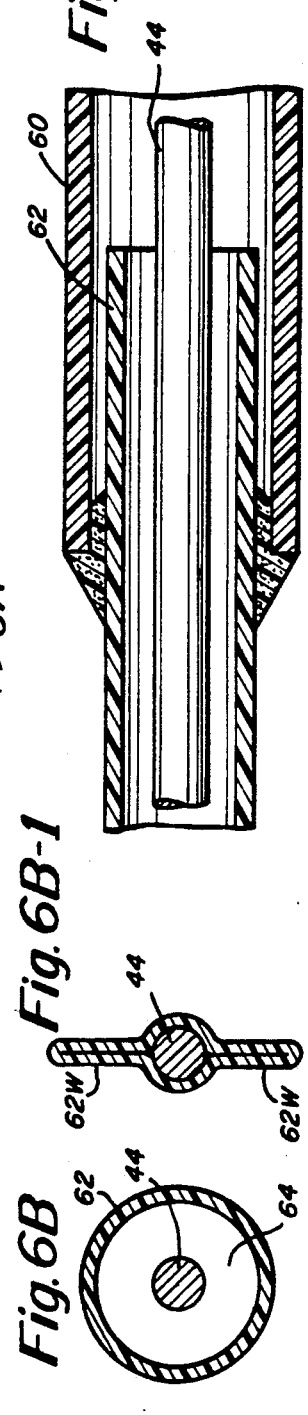

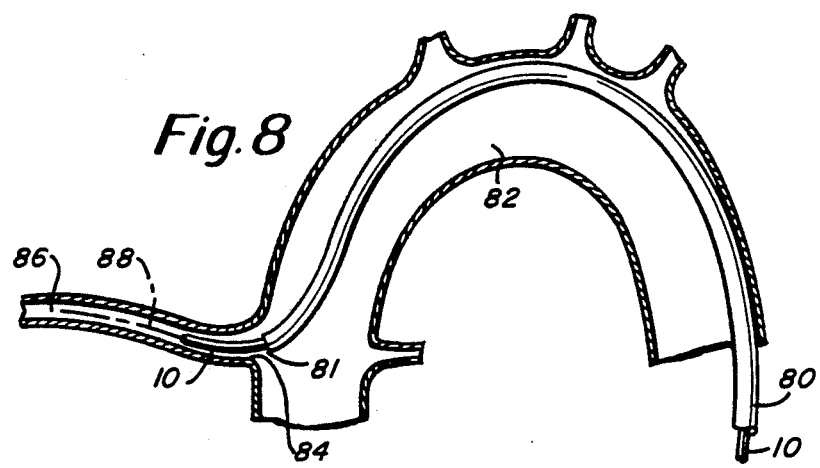
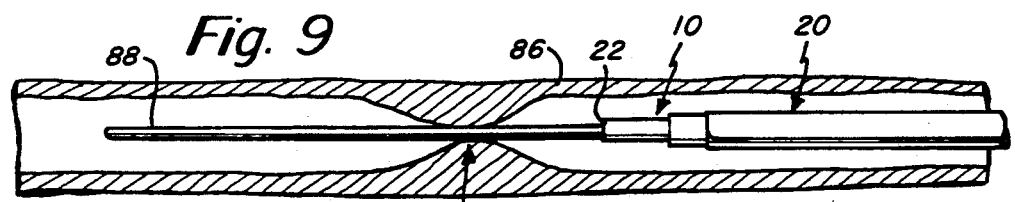
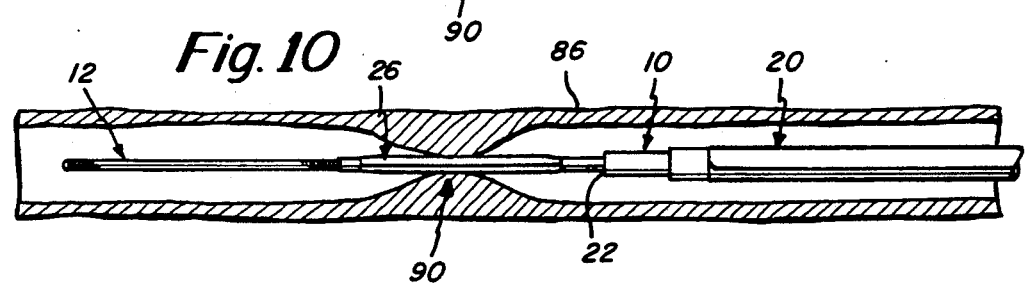
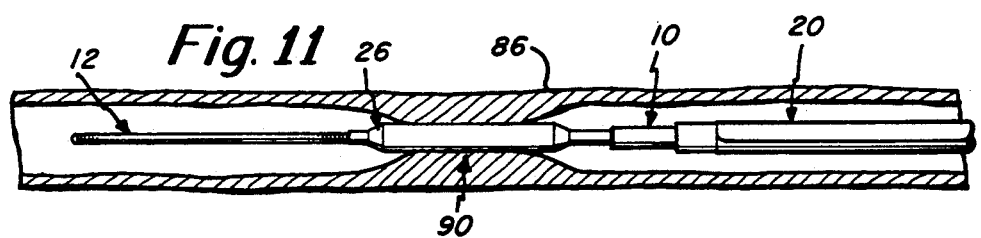
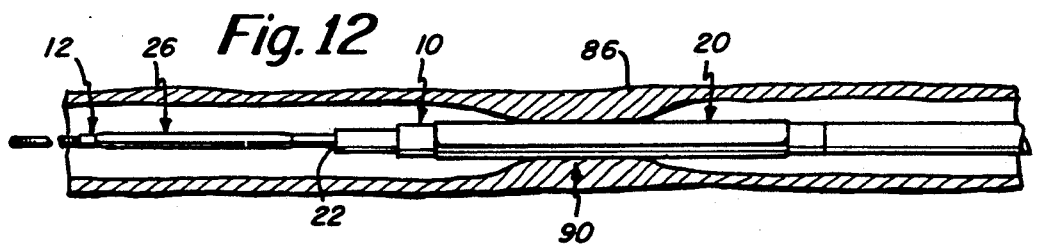
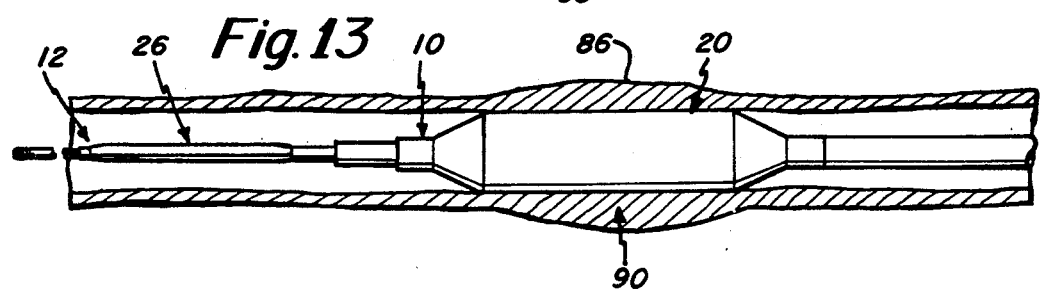

MICRODILATATION PROBE AND SYSTEM FOR PERFORMING ANGIOPLASTY IN HIGHLY STENOSED BLOOD VESSELS

FIELD OF THE INVENTION

This invention relates to new and improved catheters and systems for performing balloon angioplasty procedures on stenosed blood vessels.

BACKGROUND OF THE INVENTION

Balloon angioplasty procedures have been used in recent years with increasing success in the treatment of obstructed arteries, such as the coronary arteries. The procedure involves advancing a catheter having a special balloon at its distal end to the location of the stenosis. The balloon portion of the catheter is placed, in its deflated condition, in the stenosis and then is inflated under high pressure to compress radially and outwardly the biological material such as plaque which forms the stenosis. A balloon dilatation system of this type is illustrated in Gruntzig U.S. Pat. No. 4,195,637. In those situations in which balloon angioplasty can be used, its successful use avoids the greater risk of complex and expensive bypass surgery.

Not all arterial stenoses are treatable by balloon angioplasty. Among the types of vascular obstructions which have not been treatable with the angioplasty technology are those in which the passage through the stenosis is so narrow that the balloon angioplasty catheter cannot be inserted into the stenosis, even when the balloon is in its collapsed, deflated condition. Thus, where the opening in a stenosis was only enough to permit passage of a guide wire, but not enough to permit passage of a deflated angioplasty balloon, the procedure could not be performed. Until the present invention, such conditions disqualified the patient from receiving the potential benefits of the angioplasty technique. Instead, such conditions required bypass surgery.

Also among the difficulties encountered in the angioplasty technique has been in the advancement and placement of the dilatation balloon catheter in the intended branch of the arterial tree so that it can be advanced into the stenosis to be treated. Difficulties often are encountered in guiding the catheter to the obstructed branch or portion of the arterial tree.

It is among the primary objects of the invention to provide a dilatation catheter system including a microdilatation probe which enables such very narrow stenoses to be treated with the balloon angioplasty technique, and in a manner in which the catheter can be guided accurately.

SUMMARY OF THE INVENTION

The invention involves use of a novel probe which is advanceable through a lumen formed in the angioplasty catheter. The probe is very small in diameter and has a small diameter, thin-wall balloon at its distal portion. The balloon is expandable to a predetermined maximum diameter which is just slightly greater than the collapsed diameter of the balloon portion of the dilatation catheter.

In another aspect of the invention, the probe is constructed and arranged to be advanceable through the patient's vascular system and can be controlled and manipulated from its proximal end so that it can be steered selectively at forks in the vascular system. The steering capability coupled with the very small diameter of the probe enables it also to be used as a guide wire over which the angioplasty balloon catheter can be advanced.

In a further aspect of the invention the probe and catheter are constructed to permit fluid communication from the distal end of the catheter to the proximal end for distal pressure monitoring as well as for infusion of liquids, such as radiopaque dyes.

The main body of the probe has a flexible, elongate, hollow main shaft adapted to transmit torque without whipping. A smaller diameter balloon support wire is attached to and extends from the distal end of the flexible hollow shaft. A helical spring is mounted to the distal portion of the support wire. The microdilatation probe balloon is attached at its proximal end to the distal portion of the main shaft. An inflation/deflation port is formed in the hollow main shaft, distally of the proximal balloon connection, to communicate with the interior of the balloon for inflating and deflating the balloon. The distal end of the balloon is attached to the proximal end of the helical spring. A distal segment of the probe which projects beyond the microdilatation balloon, includes the helical spring and portion of the support wire. The support wire is tapered within the helical spring to provide progressively increasing flexibility in a distal direction. The distal end of the probe is adapted to be bent to a curve and enables the probe to be selectively directed and steered by rotating the probe from its proximal end.

The microdilatation balloon is very thin. The diameter of the collapsed, folded balloon portion of the probe is small enough to fit through the main lumen of the angioplasty catheter. In its inflated condition, the microdilatation balloon defines an outer diameter which is slightly greater than the diameter of the collapsed balloon portion of the angioplasty catheter. Additionally, the outer diametral dimensions of the probe and the inner diameter of the main lumen in the angioplasty catheter are formed to define a clearance to provide a continuous fluid passage to provide fluid communication from the proximal to the distal end of the combined probe and catheter, without requiring removal of the probe.

The invention may be used in various protocols. Where it can be determined in advance that the angioplasty catheter will not itself be able to cross the lesion, the angioplasty catheter and microdilatation probe may be preassembled and advanced, as a unit. In those instances where a guide wire was used preliminarily to serve as a guide for the angioplasty balloon and it becomes apparent that the stenosis cannot be crossed by the angioplasty catheter, the guide wire can be removed and exchanged for the microdilatation probe. The probe then is advanced through the angioplasty catheter until its distal end is projected beyond the end of the catheter. The probe balloon extension beyond the distal end of the angioplasty catheter is confirmable by a radiopaque marker arrangement on the microdilatation probe and angioplasty catheter. Once the balloon of the microdilatation probe is in the stenosis, the probe balloon is expanded to enlarge the passage through the stenosis. The balloon then is collapsed and the angioplasty catheter can be advanced over the microdilatation probe into the enlarged stenosis. The angioplasty balloon then is expanded and the dilatation procedure is completed.

It is among the objects of the invention to provide a system by which an angioplasty procedure can be performed on a stenosed blood vessel in which the lumen through the stenosis is too small to permit entry of the angioplasty catheter.

Another object of the invention is to provide an angioplasty system which can be used to dilatate a stenosis in which the opening is as small as about 0.020 inches diameter.

Another object of the invention is to provide a dilatation probe having a microdilatation balloon for performing a preliminary dilatation to open the stenosed balloon vessel to a degree large enough to receive the main angioplasty catheter.

A further object of the invention is to provide a dilatation system which utilizes a plurality of telescoping tubular members telescoped within each other, each of which has a balloon at its distal end, in which the balloon on the inner member is expandable to a diameter which is between the unexpanded and expanded diameters of the balloon on the next surrounding tube.

Another object of the invention is to provide a dilatation catheter and probe system in which a probe has a balloon which is expandable to a diameter just slightly greater than that of the collapsed balloon portion of the dilatation catheter.

Another object of the invention is to provide a microdilatation probe having an outer diameter approximately the same as the diameter of a guide wire so that the probe may be exchangeable for the guide wire without requiring catheter changes and while the angioplasty catheter remains in place.

A further object of the invention is to provide a system of the type described which allows the angioplasty procedure to be performed in cases which, before the invention, could not have been performed and would have required bypass surgery.

Another object of the invention is to provide a microdilatation probe and angioplasty catheter which maintains fluid communication from the proximal end of the catheter to the distal end while the probe is in place in the angioplasty catheter so as to permit pressure measurements and liquid infusion.

Still another object of the invention is to provide a microdilatation probe which can be manipulated from the proximal end and can be steered with control adequate to be selectively guided through a patient's arterial tree to a precise intended location.

DESCRIPTION OF THE DRAWINGS

The foregoing and other objects and advantages of the invention will be appreciated more fully from the following further description thereof, with reference to the accompanying drawings wherein:

FIG. 1 is an illustration of the balloon dilatation catheter and microdilatation probe extending through the catheter and illustrating the probe balloon and dilatation balloon in their respective deflated and inflated configurations;

FIG. 2 is a cross section taken through the balloon catheter and probe as seen along the line 2—2 of FIG. 1;

FIG. 3 is a longitudinal, fragmented illustration of the microdilatation probe;

FIG. 4 is a fragmented, longitudinal illustration, partly broken away and partly in section of the dilatation catheter;

FIGS. 4A–4C are sectional illustrations of the dilatation catheter as seen along the lines 4A—4A, 4B—4B and 4C—4C of FIG. 4, respectively;

FIG. 4C-1 is a sectional illustration of the dilatation catheter as seen along the line 4C—4C of FIG. 4, but with the probe positioned in the catheter and illustrating the configuration of the sleeve extension when inflated;

FIG. 4C-2 is an illustration similar to FIG. 4C-1 but with the sleeve extension in an evacuated, collapsed configuration;

FIG. 5 is an enlarged longitudinal section of the portion of the microdilatation probe which includes the transition region from the proximal segment to the distal segment;

FIG. 5A is a sectional illustration of the transition tube as seen along the line 5A—5A of FIG. 5;

FIG. 6 is an enlarged longitudinal sectional illustration of the balloon portion and distal segment of the microdilatation probe;

FIG. 6A is a sectional illustration of the probe balloon as seen along the lines 6A—6A of FIG. 6;

FIG. 6A-1 is an illustration of the probe balloon of FIG. 6A in an evacuated, collapsed configuration;

FIGS. 6A-2 and 6A-3 are illustrations of the collapsed probe balloon with its wings wrapped about the support wire in an S-shaped configuration and a C-shaped configuration, respectively;

FIG. 6B is a sectional illustration of the sleeve extension of the probe when the probe is in an inflated condition;

FIG. 6B-1 is an illustration of the sleeve of FIG. 6B when in an evacuated, collapsed configuration;

FIG. 7 is an enlarged sectional illustration of the juncture of the balloon and the balloon extension sleeve;

FIG. 8 is a diagrammatic illustration of the aortic arch and the position of a guide catheter and dilatation catheter in the aortic arch in readiness to perform an angioplasty procedure;

FIG. 9 is a diagrammatic illustration of a stenosed artery with a dilatation catheter and guide wire in the artery and illustrating a situation in which the dilatation catheter cannot pass through the stenosis;

FIG. 10 is a diagrammatic illustration of the microdilatation probe which has been advanced into the stenosis of FIG. 9 in readiness to perform a preliminary, partial dilatation;

FIG. 11 is a diagrammatic illustration of the microdilatation probe balloon in an inflated condition within the stenosis;

FIG. 12 is a diagrammatic illustration of the dilatation catheter being advanced over the microdilatation probe to locate the dilatation balloon within the partially enlarged stenosis; and FIG. 13 is a diagrammatic illustration of the positioned dilatation catheter with its balloon inflated.

DESCRIPTION OF THE PREFERRED EMBODIMENT

FIG. 1 illustrates a balloon dilatation catheter 10 together with the microdilatation probe 12 extending through and protruding distally beyond the catheter. The dilatation catheter 10, particularly when it is intended for use in a narrow artery, such as in a coronary artery, is slender and, for example, may have an outer diameter of the order of 0.050 inches. As shown in FIG. 2 and FIGS. 4A–4C the dilatation catheter 10 has a main body 14 through which two lumens are formed, including a main lumen 16 and a balloon inflation lumen 18. The dilatation catheter preferably is formed extruded plastic and may be formed with an internal web 15 which separates and defines the lumens 16, 18. In the illustrative embodiment, both of the lumens 16, 18 are generally D-shaped in cross section. The balloon inflation lumen 18 communicates with the interior of a dilatation balloon 20 mounted at the distal end of the catheter 10. The main lumen 16 extends fully along the length of the main body 14 of the catheter, from the proximal end of the catheter to the distal tip where it opens at an outlet opening 22. The proximal end of the dilatation catheter is provided with a Y-fitting 24 through which communication may be had with each of the main and inflation lumens 16, 18. For that purpose, separate tubes, 17, 19 branch proximally from the fitting 24. The tubes 17, 19 communicate respectively with the main lumen 16 and inflation lumen 18. Fittings, 21, 23 are provided at the proximal ends of the tubes 17, 19 for connection with syringes, pressure measuring devices and the like.

By way of dimensional example, in a dilatation catheter having an outer diameter of the order of 0.050 inches, the main lumen may be of the order of 0.022 inches in width at its smallest cross-sectional dimension. The inflation lumen 18 is of even smaller cross-sectional size, as will be described.

In performing an angioplasty procedure, the dilatation catheter 10 is advanced through the patient's arterial system to locate the dilatation balloon in the narrowed lumen of the arterial obstruction. The dilatation balloon 20 then is inflated under substantial pressure to enlarge the diameter of the lumen and to cause radial outward compression of the plaque which caused the obstruction. The dilatation catheter 10 may be advanced to the arterial site to be treated through a guide catheter. A guide wire also may be used to advance and guide the catheter. The guide wire is receivable in the main lumen 16 of the catheter 10 and is extended beyond the distal end of the catheter 10. The use of a guide wire enables the dilatation catheter 10 to be advanced over the guide wire to narrower, more distal portions of the arterial tree than can be achieved with the use of a guiding catheter alone.

Among the difficulties which may arise in angioplasty procedures is that although the dilatation catheter may be advanced to the location of the stenosis, the passageway through the stenosis is too small to permit the collapsed balloon portion of the dilatation catheter 10 to be inserted into the stenosis. Thus, although the passageway through the stenosis may have been large enough to permit passage of a guide wire, the dilatation catheter could not be positioned to perform the angioplasty procedure. Under those circumstances, the patient typically was required to undergo an immediate and extensive surgical procedure, such as a coronary bypass operation. The present invention provides a system and technique by which such the angioplasty procedure can be performed under such circumstances, thereby avoiding the necessity of bypass surgery.

As shown in FIG. 1 the microdilatation probe 12 is of very slender construction and can be passed through the main lumen 16 of the dilatation catheter 10 so that the distal end of the probe 12 can protrude through the outlet opening 22, and extend distally beyond the dilatation catheter 10. The probe is illustrated in phantom in FIG. 2 to show its relative size and shape with respect to the main lumen 16. When the probe, having a circular cross section, is disposed in the main lumen 16 there will be substantial voids through the main lumen 16, on opposite sides of the probe, through which fluids may be administered to the patient and through which blood pressure measurements may be taken. As will described in further detail, the fluids may be administered and the pressure measurements may be taken without removing the probe 12 at all, thereby enabling the angioplasty procedure to proceed quickly. By way of example, the cross section taken up by the outer diameter of the probe 12 preferably is of the order of no more than about 50 or 60 percent of the cross sectional area of the main lumen 16.

The microdilatation probe 12 has a balloon 26 which, when collapsed, defines a small enough cross-sectional configuration that it can be advanced through the main lumen 16 of the dilatation catheter. The diameter of the probe balloon 26, when fully inflated is just slightly greater than the outer diameter of the dilatation catheter 10 when the catheter balloon 20 is deflated. In its collapsed configuration the probe balloon 26 as well as the remaining portions of the probe 12 define an outer diameter corresponding to that of the guide wire. As will be described in further detail, when the dilatation catheter 10 cannot be advanced into the lumen of the stenosis, the microdilatation probe 12 can be passed through the main lumen 16 of the dilatation catheter 10 to locate the collapsed probe balloon 26 within the stenosis. The probe balloon 26 then is inflated to enlarge the passageway through the stenosis to a size which will be able to receive the dilatation catheter 10. The probe balloon 26 then is deflated and the balloon dilatation catheter 10 then is advanced into the stenosis to complete the angioplasty procedure.

The microdilatation probe 12, illustrated in FIG. 3, is longer than the dilatation catheter 10. For example, with a dilatation catheter having a length of approximately 150 centimeters the overall length of the probe 12 preferably is of the order of about 180 centimeters. The respective lengths of the probe 12 and catheter 10 should be such that the probe can be manipulated from its proximal end so that the probe balloon 26 is extended distally and completely out of the outlet opening 22 of the dilatation catheter 10.

The probe 12 has a relatively long proximal segment 28 which is formed from narrow, solid wall tubing, such as hypodermic tubing. In the illustrative embodiment, the proximal segment 28 may be of the order of 150 centimeters long, about as along as the dilatation catheter 10. The proximal segment 28 is rigid torsionally so that it can transmit substantially fully to its distal end rotational motion imparted to the proximal end. As will be described, the distal tip of the probe can be bent to a preset curve. Rotation applied to the probe can be controlled to selectively direct and steer the curved distal end of the probe as it is advanced. The proximal segment 28 also is flexible and can bend longitudinally to follow the curvature of the patient's arterial system. Preferably the proximal segment 28 of the probe 12 is sufficiently flexible that it can bend to follow the curve of a patient's aortic arch which has a radius of the order of between 2.5 to 3.5 inches in an adult.

As shown more clearly in enlarged FIG. 5, in the preferred embodiment of the invention the hollow tubular segment 28 has an outer diameter of 0.018 inches, a wall thickness of about 0.002 inches and an internal diameter passage 30 of 0.014 inches. A conventional fitting 32 is secured to the proximal end of segment 28 to facilitate connection with an inflation/deflation device, such as a syringe (not shown).

The probe 12 includes a distal segment 34 which extends from the distal end of the proximal segment 28 to the distal end of the probe 12. The distal segment 34 includes a narrow diameter elongate support wire 44 which is connected to and extends distally of the proximal segment 28. The support wire 44 is connected to the proximal tubing 28 by a short transition tube 36. The transition tube 36 is about one-half inch long and also is formed from slender, flexible hypodermic tubing with a smaller diameter than the proximal tube 28, In the illustrative embodiment, the transition tube 36 is formed from hypodermic tubing having an outer diameter of 0.014 inches, a wall thickness of 0.003 inches and an inner diameter of 0.008 inches. The proximal end of the tubing 36 is received within the distal end of the internal passage 30 of the proximal segment 28 and is secured thereto as by soldering or brazing. The solid support wire 44 is attached to the distal end of the transition tube 36. The wire 44, which in the illustrative embodiment is very slender, preferably 0.008 inches diameter, is received in the distal end of the passage 38 of the tubing 36 and is secured by soldering or brazing. The support wire 44 plugs the distal end of the tubing 36. In order to permit the balloon 26 to be inflated and deflated, the transition tube 36 is provided with apertures 46 on opposite sides of the tube wall to provide communication with the internal passages 38, 30 of the probe. The apertures 46 may be defined by forming a pair of longitudinal slots in the wall of the tubing 36. The support wire 44 provides support for the probe balloon 26 and also extends distally beyond the balloon 26, to form the core of a leader segment 48. The leader segment includes a helically wound radiopaque coil spring 50 which is attached to the distal end of the core wire 44 in a manner described below.

The probe balloon 26 is formed by molding high strength polymeric material in a manner which provides a thin balloon wall not greater than about 0.001 inches thickness and, preferably, having a thickness of the order of 0.0005 inches. The balloon may be manufactured as described in U.S. Pat. No. 4,490,421 issued Dec. 25, 1984 and reference is made thereto for further details concerning the manufacture of the balloon.

As shown in enlarged detail in FIG. 6, the balloon includes a main cylindrical portion 52 which, in its fully inflated configuration defines an outer diameter just slightly greater than the outer diameter of the dilatation catheter 10 with its balloon 20 collapsed. In the illustrative embodiment, the probe balloon 26 preferably has an outer diameter of 1.3 millimeters. As mentioned above, the balloon is formed from a high strength material which will not tend to stretch when inflated. The length of the balloon 26 may be of the order of 15 millimeters. The balloon is formed to include tapering portions 54, 56 at the proximal and distal ends respectively. The distal tapering portion 56 merges into a narrowed neck 58 which fits snugly about and against the proximal end of the coil spring 50. The distal neck 58 of the probe balloon 26 is adhesively attached to the coil spring 50. As will be described in further detail, the proximal end of the coil spring is soldered securely to the core wire at the region where the distal neck 58 of the probe balloon 26 is joined. The proximal tapering portion merges into a narrowed proximal neck 60.

In order to communicate the interior of the probe balloon 26 with the inflation/deflation passages 30, 38 of the tubing, an extension sleeve 62 is adhesively attached to the proximal neck 60. The extension sleeve 62 extends proximally over the support wire 44. The proximal end of the extension sleeve 62 preferably is formed from the same material as the balloon 26 and is securely and adhesively attached to the outer surface of the transition tube 36, where it joins the main tube 28. The extension sleeve 62 defines an annular passage 64 about the support wire 44. The annular passage 64 provides communication between the apertures 46 and the interior of the balloon 26 for inflation and deflation of the balloon.

As shown in FIG. 6 the leader segment 48 which extends distally of the balloon 26 is of increasing flexibility in a distal direction to provide a relatively soft, flexible leading tip which reduces the chance of trauma or injury to the blood vessel. In the illustrative embodiment the leader segment is about 3 centimeters long. The coil spring 50 is soldered, at its proximal end to the support wire 44, as indicated at 66. The distal end of the support wire 44 also is soldered to the coil spring 50 as indicated at 68. Soldered joint 68 and the distal tip of the support wire 44 terminate short of the distal tip 69 of the coil spring 50. The distal tip 70 of the coil spring 50 may extend about five millimeters beyond the soldered joint 68 and defines a highly flexible bumper tip. A rounded weld bead 67 is formed at the distal tip of the spring 50. The leader segment 48 is of increasing flexibility in a distal direction. The support wire 44 is taper ground and, for example, may be ground smoothly to a 0.002 inch diameter at its distal tip 69.

The distal tip 70 of the coil spring 50 includes a flexible and bendable stainless steel shaping ribbon 71 which is secured to the distal tip 69 of the support wire at one end, and to the distal weld bead 67 at its other end. The shaping ribbon is of slender, rectangular cross section, of the order of 0.001 inches by 0.002 inches. The shaping ribbon is adapted to be bent to a desired curve and to retain that curve when relaxed. The preset curve enables the probe 12 to be steered by rotation of the probe from its proximal end. The probe can be rotated to direct the prebent distal tip 70 in selective directions as desired within the patient's blood vessels.

The probe also is provided with a radiopaque marker band 72 which preferably is formed from platinum. The marker band 72 is located proximally of the main portion of the balloon 26. In the illustrative embodiment it is securely attached to the support wire 44. The marker band 72 provides a means by which the physician can verify, fluoroscopically, that the probe balloon 26 has been extended beyond the outlet opening 22 of the dilatation catheter 10, as a precaution before the probe balloon 26 is inflated.

The microdilatation probe 12 is constructed so that it can pass through the main lumen 16 of the dilatation catheter but without blocking off fluid communication along the main lumen 16. That enables the advantages of the microdilatation probe to be used without compromising the fluid infusion and pressure monitoring capabilities of the dilatation catheter 10. As shown in FIGS. 4, 4A, 4B and 4C, the main lumen 16 of the dilatation catheter varies in cross sectional dimensions and shape, particularly through the distal region of the catheter which contains the balloon 20. For example, the D-shaped main lumen 16 as seen at the section indicated at FIG. 4A is dimensioned to be 0.028 inches high and 0.036 inches wide. The main lumen 16 narrows at the section indicated at FIG. 4B to 0.024 inches high by 0.032 inches wide. The main lumen 16 then makes a transition to a circular shape and, as indicated at the section at FIG. 4C, the diameter may be 0.022 inches. At the distal outlet opening 22 of the dilatation catheter the diameter of the main lumen 16 is still further reduced, to about 0.020 inches.

Among the difficulties presented when attempting to pass a member through the very narrow main lumen 16 of the catheter 10 is that the member will tend to restrict fluid flow communication through the main lumen, from the proximal to the distal end of the catheter. The microdilatation probe, having a main body diameter of 0.018 inches provides sufficient clearance within the main lumen 16, particularly at the sides of the D-shaped cross section of the lumen to permit quite adequate fluid communication. In the more distal portions of the catheter 10, such as at the portion indicated by the cross section of FIG. 4C, the narrowed lumen 16 provides less clearance for fluid communication. In order to maximize fluid communication through the lumen 16 when the probe 12 is in place, particularly through the more narrowed portions of the lumen 16, the distal segment 34, and particularly the portion of the distal segment 34 which is proximal of the balloon 26, embodies a construction which assures that a sufficiently large flow area will be maintained throughout the main lumen 16 of the catheter 10. To that end, the support wire 44 and sleeve extension 62 are constructed so that when the probe is deflated, the sleeve extension 62 will collapse to a very small cross sectional area which will not adversely obstruct the main lumen 16 of the catheter 10, even in the more narrowed regions of the main lumen 16. Additionally, the length of the distal segment 34, proximally of the balloon 26 is sufficiently long, about twenty centimeters, so that the proximal segment 28 need not be inserted into the more narrowed portions of the catheter lumen 16. Even when the probe 12 is advanced through the catheter 10 to extend to its maximum distance beyond the outlet 22 of the catheter 10, the distal end of the proximal tubing 28 will remain proximal of the balloon 26.

When the microdilatation probe is in use and its balloon 26 is extended distally beyond the outlet 22 of the catheter 10 the narrowed portion of the main lumen, in the region of the dilatation balloon 20 will be occupied by the narrow support wire 44 and surrounding extension sleeve 62. When the probe balloon 26 is inflated, the sleeve 62 will be expanded to its full diameter, of the order of 0.017 inches. As illustrated in FIG. 4C-1, when the extension sleeve 62 is inflated to its diameter of about 0.017 inches, only a relatively small annular portion of the main lumen 16 is available for fluid flow communication. Thus, during the interval when the probe balloon is inflated, the ability to infuse liquids and to take pressure measurements is somewhat reduced. However, when the probe balloon is deflated, by applying suction to the probe, the sleeve extension 62 collapses about the slender support wire 44, as suggested in FIG. 4C-2. The sleeve 62 collapses in a manner which tends to form flattened wings 62W which may curl against the inner wall of the lumen 16, as suggested in FIG. 4C-2. When in the collapsed configuration illustrated in FIG. 4C-2, there is a very substantial open flow area through the lumen 16 which permits full and free liquid infusion and pressure measurement, as desired. Because the probe balloon 26 is inflated only very briefly during the entire procedure, and is deflated, as shown in FIG. 4C-2 for most of the time, the system displays the desired capability of liquid infusion as well as pressure measurement.

In order that the probe may be passed through the main lumen 16 of the dilatation catheter, the probe balloon 26 also must be collapsible to a shape and size which can be passed through the main lumen 16. The invention accomplishes these objectives by using the slender, small diameter support wire 44 extending through the balloon and by using a balloon with a very thin but high strength wall. When the microdilatation probe 12 is to be inserted through the catheter, the balloon 26 first is collapsed by applying suction, such as by a syringe, to the fitting 32. The balloon 26 and the extension sleeve 62 collapse, tending to form radially projecting wings as illustrated in FIGS. 6A-1 and 6B-1, respectively. The wings 62W and 26W wrap about the support wire 44 when the probe is advanced through the main lumen 16 of the dilatation catheter 10. The wings 26W may wrap about the core wire 44 either in an S-shaped configuration suggested in FIG. 6A-2 or in a C-shaped configuration shown in FIG. 6A-3. In either configuration the overall diameter through the collapsed and folded balloon portion of the probe 12 includes six layers of the balloon material in addition to the diameter of the support wire 44. In accordance with the present invention, the balloon is formed from a high strength thin material having a wall thickness preferably not more than about 0.001". Thus, the aggregate diameter of six balloon layers plus the support wire is about 0.014 inches. The probe balloon thus is collapsible to a diameter which is about one fourth of its inflated diameter and which can pass easily through the main lumen 16 of the dilatation catheter 10 even in the more restricted portions which may have a diameter of the order of 0.022".

The manner in which the system is used is illustrated in FIGS. 8-13. As suggested diagrammatically, a guide catheter 80 is inserted initially in the patient's arterial system, usually through the femoral artery and is advanced through the aortic arch 82 to locate the distal tip 81 of the guide catheter at the coronary ostium 84 leading to the coronary artery 86 to be treated. The guide catheter 80 typically is too large to be inserted into the coronary artery 86 and serves only to provide a path which leads the dilatation catheter 10 to the coronary artery 86. After the guide catheter has been positioned the dilatation catheter 10 is advanced through the guide catheter 80 with its dilatation balloon 20 collapsed. When the dilatation catheter projects out of the tip 81 of the guide catheter it can be advanced into the coronary artery 86. Under fortuitous conditions the dilatation catheter 10 may be advanceable in that manner to locate the inflation balloon 20 within the stenosis. The balloon 20 then may be expanded and the dilatation procedure completed, after which the dilatation catheter 10 and guide catheter 80 can be removed.

It may be preferable in some procedures to introduce the dilatation catheter together with a guide wire indicated diagrammatically and in phantom at 88. In that protocol the guide wire 88 is inserted into the dilatation catheter 10 and the two are advanced, as a unit, through the guide catheter 80. When the coronary ostium is 84 reached, the guide wire 88 may be advanced into the coronary artery 86 and may be manipulated in an effort to advance the guide wire into the branch of the arterial tree in which the stenosis is located. Once the guide wire has been advanced through the stenosis, the dilatation catheter is advanced over the guide wire which guides it directly to the stenosis.

FIG. 9 is a diagrammatic illustration of a dilatation catheter 10 which has been advanced over a guide wire 88 through the artery 86 to the stenosis. In the embodiment illustrated in FIG. 9 the opening through the stenosis 90 is large enough to permit the guide wire 88 to pass but is not large enough to permit entry of the distal end of the dilatation catheter 10. As described above, before the present invention, this situation was not treatable by angioplasty and typically was treated immediately with bypass surgery.

In accordance with the present invention, however, the surgeon can withdraw the guide wire 88 while maintaining the dilatation catheter 10 in place. The microdilatation probe 12 then is substituted for the guide wire 88 and is advanced through the main lumen 16 of the dilatation catheter 10. The microdilatation probe 12 is advanced with its balloon 26 in a collapsed configuration illustrated in either of FIGS. 6A-2 or 6A-3. The diameter of the microdilatation probe 12 is about the same as the guide wire 88. The probe 12 thus can be advanced out of the distal opening 22 of the catheter 10 and the balloon 26, in its collapsed configuration, can be inserted into and through the stenosis 90 as suggested in FIG. 10. Once it has been verified that the probe balloon 26 is within the stenosis 90 and is fully out of the main lumen 16 the probe balloon 26 can be inflated under pressure to expand forcefully the probe balloon 26 to its maximum diameter thereby making a preliminary enlargement of the passageway through the stenosis. FIG. 11 is an illustration of the dilatation probe in its expanded configuration within the arterial stenosis 90. As can be seen, the balloon 26 has been inflated to enlarge the passage through the stenosis to a diameter just large enough so that it will be able to receive the distal end of the dilatation catheter 10.

It is important that the probe balloon 26 is not inflated until after it has been extended distally beyond the end of the dilatation catheter 10. A marker band 72 on the probe provides a means by which it can be verified that the probe balloon has been extended out of the outlet opening. As shown in FIG. 4 the dilatation catheter 10 has a pair of marker bands 74, 76 located adjacent the proximal and distal ends, respectively, of the dilatation balloon 20. The position of the probe can be verified fluoroscopically. When the marker band 72 on the probe is located sufficiently distally of both marker bands 74, on the catheter, that indicates proper extension of the probe 12 and readiness to inflate the probe balloon 26.

When the probe balloon 26 has been inflated to enlarge the opening through the stenosis 90 the probe balloon 26 is collapsed by aspirating the probe. With the balloon 26 evacuated the dilatation catheter can be advanced over the microdilatation probe 12 which then serves the function of a guide wire to guide the dilatation catheter (FIG. 12). The dilatation catheter then can be advanced over the probe to locate the dilatation balloon 20 within the partially dilatated stenosis. The dilatation balloon 20 then is inflated as suggested in FIG. 13 to complete the angioplasty by compressing the stenotic material radially outwardly. With the coronary lumen thus enlarged the dilatation balloon 20 is deflated. The dilatation catheter 10 and probe 12 then are removed to leave the artery with an enlarged flow area where it had been previously stenosed.

Modifications may be made to the procedure with respect to the relative positioning of the probe and catheter after the preliminary dilatation has been performed. In some instances the surgeon may prefer to advance the probe and catheter in unison without any relative movement between the two, when advancing the dilatation balloon 20 into the preliminarily dilatated stenosis. In other instances there may be special considerations resulting in a decision not to advance the probe while advancing the dilatation catheter into the stenosis. That protocol, too, is available with the present invention, by collapsing the probe balloon which then will wrap to a compacted configuration as the dilatation catheter is advanced over that portion of the probe.

As described above, one of the features of the probe 12 is the increased flexibility of the distal segment 34 of the probe. The proximal segment 28, as described, is sufficiently flexible so that it can bend relatively easily through the aortic arch (see FIG. 8). The bend from the aorta, into the coronary ostium 84 and thereafter through the coronary arteries are sharper and shorter radiused. The length of the more flexible distal segment 34 is sufficient so that the probe balloon can reach deeply into the arterial tree without requiring the stiffer proximal tubing 28 to pass through relatively sharp bends, such as the bend from the guide catheter to the coronary ostium. The distal segment 34, which consists substantially of the thin, flexible support wire 44 is able to make the relatively sharp bends with ease. Thus, the only portion of the probe 12 which actually enters the coronary artery is that which includes the slender support wire 44. This support wire is very flexible and is more easily bent to be able to negotiate shorter radius bends encountered in the coronary arterial tree.

In some instances it may have already been determined, by angiography that the stenosis to be treated is so narrow that it is unlikely that the dilatation catheter 10 will be able to pass through the stenosis. Under those circumstances it may be desirable to forego the use of a separate guide wire and, instead, insert the dilatation catheter with the microdilatation probe already in place within the catheter, so that the probe 12 can serve as a guide wire. When used in that manner it should be understood that the probe is far more steerable than conventional guide wires which have been used in the past. The steerable characteristic of the probe is due in large measure to the solid wall of the tubing in the elongate proximal segment 28 of the probe. The tubing is substantially torsionally rigid and tends to transmit substantially all of its rotation applied at the proximal end to the distal end. Although the intermediate segment of the probe, which includes the slender 0.008 inch diameter wire is too small a diameter to effectively transmit torque over relatively long distances, the distal segment 34 is relatively short, preferably about twenty-five centimeters and, therefore, does not have too great of an adverse effect on the torque transmission from the proximal end of the probe to the distal end. The distal segment preferably is no longer than about 25 centimeters, as compared to the solid wall tubular proximal segment which is approximately 150 centimeters long. Thus, by forming a bend in the distal tip 70 of the leading segment, the direction of the probe 12 can be controlled by rotating the probe from the proximal end.

From the foregoing it will be appreciated that the invention provides a system and method by which the angioplasty technique for treating arterial stenoses can be extended to certain stenoses which previously required bypass surgery. The system enables a microdilatation probe to be advanced through the dilatation catheter while maintaining fluid communication from the proximal to the distal end of the dilatation catheter even while the probe is in place. Moreover, the invention provides these advantages with a probe which can be steered to selectively guide through the branches of a patient's arterial tree and in which the probe can be substituted for a guide wire.

It should be understood, however, that the foregoing description of the invention is intended merely to be illustrative thereof and that other modifications and embodiments of the invention will be apparent to those skilled in the art without departing from its spirit.

Having thus described the invention what I desire to claim and secure by letters patents is:

1. An apparatus for performing angioplasty comprising:
   a dilatation catheter having a dilatation balloon at its distal end, an inflation lumen extending from the proximal end to the balloon and main lumen extending from the proximal end and having an outlet opening at the distal end;
   a microdilatation probe having a balloon at its distal region and an inflation lumen extending through the probe to communicate the interior of the probe balloon with the proximal region of the probe, thereby to enable the probe balloon to be inflated and deflated;
   the probe being dimensioned to be passed through the main lumen of the dilatation catheter to enable the probe balloon to be extended distally beyond the distal end of the dilatation catheter; and
   the inflated diameter of the probe balloon being no smaller than the uninflated diameter of the distal region of the dilatation catheter.

2. An apparatus as defined in claim 1 where in the inflated diameter of the probe balloon is slightly larger than that of the uninflated distal region of the dilatation catheter.

3. An apparatus as defined in claim 1 further comprising, in combination:
   a guide wire passable through the main lumen of the dilatation catheter;
   the probe being substantially the same cross sectional diameter as the guide wire and being exchangeable therefore through the main lumen of the dilatation catheter.

4. An apparatus as defined in claim 1 further comprising:
   the portion of the probe extending from its proximal end to the probe balloon being longer than the total length of the dilatation catheter;
   the main lumen and the probe having a relative cross sectional areas sufficient to define a clearance there between within the main lumen, said clearance being sufficient to enable the taking of pressure measurements and the infusion of liquids through the main lumen while the probe is contained within the lumen, and without requiring removal of the probe from the lumen.

5. An apparatus as defined in claim 1 further comprising means for verifying the position of the probe balloon with respect to the distal end of the dilatation catheter thereby to facilitate determination of when the probe balloon has been extended distally beyond the distal end of the dilatation catheter.

6. An apparatus as defined in claim 5 wherein said means for verifying comprises radiopaque marker means on each of the probe and the catheter of enable fluoroscopic determination of the relative positions of the probe and catheter.

7. An apparatus as defined in claim 6 wherein said radiopaque marker means comprises:
   a pair of radiopaque markers mounted on the dilatation catheter to indicate the proximal and distal regions of the dilatation balloon; and
   at least one radiopaque marker on the probe adjacent the proximal end of the probe balloon.

8. An apparatus as defined in claim 1 further comprising:
   said probe having a proximal segment and a distal segment;
   the distal segment being more flexible than the proximal segment;
   the probe balloon being mounted to the distal segment;
   the region of transition of the probe from the proximal segment to the more flexible distal segment being located along the probe in a position in which the transition region will be contained within the main lumen of the dilatation catheter when the probe is advanced fully within the dilatation catheter whereby only the flexible distal segment of the probe may extend out of the distal tip of the dilatation catheter.

9. An apparatus as defined in claim 8 further comprising:
   said distal segment comprising a slender, flexible wire having a diameter smaller than the outer diameter of the proximal segment;
   the wire extending through the probe balloon;
   the probe balloon being thin-walled and collapsible in a manner to enable the balloon to fold to define six layers of balloon wall which have an aggregate diameter, together with a diameter of the support wire, which is smaller in cross section than the cross section of the main lumen of the catheter to enable the collapsed probe balloon to advance through the main lumen.

10. An apparatus as defined in claim 1 further comprising:
    said probe having a proximal segment and a distal segment, the distal segment being more flexible than the proximal segment;
    the proximal segment being sufficiently flexible to bend and be advance through the aortic arch;
    said apparatus further comprising a coronary guide catheter having a distal tip and being constructed and arranged to enable the distal tip to be placed at a coronary ostium;
    the length of the distal segment of the probe being sufficient so that when the probe is within the guide catheter the distal segment of the probe can be projected distally of the tip of the guide catheter sufficiently far as to be capable of reaching any portion of the coronary artery having an inner diameter large enough to receive the distal segment of the probe.

11. An apparatus as defined in claim 10 wherein the distal segment of the probe is not longer than about 25 centimeters.

12. An apparatus as defined in claim 4 further comprising:
    said probe having proximal and distal segments, the distal segment including a slender wire, the probe balloon being mounted about the wire along a distal region of the wire;

a balloon extension sleeve connected to the proximal end of the balloon and extending proximally therefrom along the distal segment and about the support wire;

the proximal end of the sleeve being in communication with and defining a portion of the probe balloon inflation lumen;

said sleeve being formed from thin, high strength material and being collapsible about the support wire;

the inflated diameter of the sleeve portion being no greater than the diameter of the proximal segment of the probe;

said sleeve being collapsible to a configuration which is wrapped about the support wire and defines a pair of flattened wings, the cross sectional area defined by the collapsed sleeve being sufficiently small as to leave a substantial cross sectional fluid flow area through the main lumen.

13. An apparatus as defined in claim 1 further comprising:

said probe having a proximal segment and a distal segment, the probe balloon being mounted to the distal segment;

the proximal segment comprising a solid wall elongate, flexible tube being adapted to transmit substantially fully to its distal end rotational movement applied at the proximal end;

the proximal segment comprising the major portion of the length of the probe;

the portion of the distal segment which extends distally beyond the balloon comprising a leader segment, the distal portion of the leader segment being bendable to a set curve;

said distal segment being sufficiently short so that it can transmit substantially the torque applied to it through the proximal segment;

whereby the bent distal tip of the probe may be directionally controlled by rotational motion applied to the proximal end of the proximal segment of the probe.

14. An apparatus for performing angioplasty comprising:

a plurality of elongate flexible telescoped shafts, including at least an innermost shaft and an outermost shaft, each of the shafts about the innermost shaft having lumens formed therethrough;

each of the shafts having a distal region and having an expandable and collapsible substantially inelastic angioplasty balloon at its distal region;

the balloon on each of the shafts, except for the outermost shaft, being expandable to a maximum diameter which is no smaller than the unexpanded diameter of the next outermost shaft and which is smaller than the expanded diameter of the balloon of the next outermost shaft;

each balloon being constructed to be collapsible to a configuration in which it can be passed through the lumen of the next outermost shaft.

15. A method for performing an angioplasty procedure with a balloon dilatation catheter in a stenosis having an opening too small to receive the dilatation catheter, said catheter having a main lumen extending therethrough and an inflation lumen, the method comprising:

providing a probe having a balloon at its distal end, the probe being of a cross sectional diameter as to be receivable through the main lumen of the dilatation catheter, the probe balloon being collapsible to an effective cross sectional area sufficient to enable it to be passed through the main lumen of the dilatation catheter;

advancing the probe, with its balloon in a deflated condition, into the stenosis to locate the deflated probe balloon within the stenosis;

thereafter inflating the probe balloon to a diameter which is not smaller than the diameter of the uninflated dilatation balloon, to enlarge the lumen through the stenosis to a diameter sufficient to permit the dilatation catheter to be inserted into the stenosis;

thereafter deflating the probe balloon and then advancing the dilatation catheter to position its balloon within the enlarged lumen of the stenosis; and thereafter inflating the dilatation balloon.

16. A method as defined in claim 15 further comprising measuring the pressure within the blood vessel at a location distal of the dilatation catheter while the probe is in place in the main lumen of the dilatation catheter.

17. A method as defined in claim 15 further comprising infusing liquid through the main lumen of the dilatation catheter while the probe is in place in the main lumen of the dilatation catheter.

18. A method as defined in claim 15 wherein said liquid comprises radiopaque dye.

19. A method as defined in claim 15 wherein said probe is inserted as a unit together with the dilatation catheter.

20. A method as defined in claim 15 wherein said catheter is inserted into the blood vessel with a guide wire located in the main lumen of the catheter; and thereafter exchanging said probe for said guide wire.

21. A method as defined in claim 15 wherein said step of advancing said dilatation catheter comprises:

a first extending said probe independently to a more distal location in the blood vessel and then advancing the dilatation catheter over the probe to use the probe as a guide.

22. A method as defined in claim 15 wherein said step of advancing said dilatation catheter comprises advancing the dilatation catheter and probe in unison without imparting relative movement between the dilatation catheter and probe.

23. A method as defined in claim 15 wherein said step of advancing the dilatation catheter comprises:

maintaining the probe in a fixed position and advancing the dilatation catheter over the probe thereby to use the probe as a guide.

24. A method as defined in claim 15 wherein said probe is constructed and arranged to transmit substantial torque from the proximal end to the distal end, and wherein said step of advancing said probe further comprises:

forming a bend in the distal tip of the probe; and advancing the probe through the blood vessel while controlling the direction of the bent distal tip of the probe by rotation from the proximal end of the probe, thereby to steer the distal end of the probe within the patient's vasculature.

25. A method as defined in claim 24 further comprising injection dye through the main lumen of the dilatation catheter to visualize the arterial anatomy while the probe is in place within the main lumen of the dilatation catheter.

26. A method as defined in claim 15 wherein said probe has a flexible distal segment on which the probe balloon is mounted, said method further comprising:

as a preliminary step, placing a guide catheter within the patient to locate the distal tip of the guide catheter at the coronary ostium of the coronary artery to be treated;

then advancing the dilatation catheter through the guide catheter and into the artery;

advancing the probe through the beyond the tip of the guide catheter and distal catheter and into the artery to an extend in which only the distal segment of the probe extends distally of the tip of a guide catheter.

27. In a dual dilatation catheter assembly for dilating a stenosis in a vessel, a first dilatation catheter, comprising a tubular element having a main lumen extending therethrough, a second tubular lumen extending longitudinally within the tubular element and forming an inflation lumen, a balloon carried by the tubular element at its distal end and having its interior in communication with the inflation lumen, a second dilatation catheter extending through the main lumen in the tubular element of the first dilatation catheter, a flexible elongate tubular element having a lumen extending therethrough, an inflatable balloon carried by the flexible tubular element of the second dilatation catheter, and having its exterior in communication with the lumen of the flexible tubular element of the second dilatation catheter, the balloon of the second dilatation catheter being elongate and having a diameter when inflated capable of dilating a stenosis, the balloon of the second dilatation catheter having a collapsed diameter which is less than the interior diameter of the lumen of the tubular element of the first dilatation catheter whereby the second dilatation catheter can be inserted and removed from the first dilatation catheter.

28. In a method for dilating stenoses in blood vessels having very small openings therein utilizing a dual dilation catheter assembly comprised of a first balloon dilatation catheter having a lumen extending therethrough and a second balloon dilatation catheter of a size which is adapted to extend through the lumen in the first balloon dilatation catheter, introducing the first dilatation catheter into the vessel so that the distal extremity of the first balloon dilatation catheter is in the vicinity of the stenosis, introducing the second balloon dilatation catheter into the first balloon dilatation catheter so that the distal extremity extends beyond the distal extremity of the first balloon dilatation catheter, advancing the second balloon dilatation catheter through the stenosis so that the balloon of the second balloon dilatation catheter assembly is disposed in the stenosis, inflating the second balloon dilatation catheter to dilate the stenosis, removing the second dilatation catheter from the stenosis, advancing the first dilatation catheter through the stenosis so that the balloon of the first balloon dilatation catheter is positioned in the stenosis, inflating the balloon of the first balloon dilatation catheter, and removing the first balloon dilatation catheter from the stenosis, and removing the first and second balloon dilatation catheters from the vessel.

* * * * *